United States Patent [19]

Müller et al.

[11] Patent Number: 4,914,124

[45] Date of Patent: Apr. 3, 1990

[54] N-ORGANOOXYCARBAMIC ACID ESTERS FOR COMBATING ENDOPARASITES

[75] Inventors: Nikolaus Müller, Monheim; Peter Andrews, Wuppertal, both of Fed. Rep. of Germany

[73] Assignee: Bayer Aktiengesellschaft, Leverkusen, Fed. Rep. of Germany

[21] Appl. No.: 147,469

[22] Filed: Jan. 25, 1988

[30] Foreign Application Priority Data

Feb. 3, 1987 [DE] Fed. Rep. of Germany ....... 3703106
May 19, 1987 [DE] Fed. Rep. of Germany ....... 3716685
Sep. 16, 1987 [DE] Fed. Rep. of Germany ....... 3731052

[51] Int. Cl.⁴ ............................................. A01N 47/24
[52] U.S. Cl. .................... 514/478; 514/452; 514/463; 514/466; 514/481; 514/489; 514/490; 549/366; 549/438; 558/417; 560/133; 560/134; 560/135; 560/136; 560/137
[58] Field of Search ............... 514/478, 481, 489, 490, 514/452, 465, 466, 463

[56] References Cited

FOREIGN PATENT DOCUMENTS 1034049 6/1966 United Kingdom ................ 514/478

Primary Examiner—Michael L. Shippen
Attorney, Agent, or Firm—Sprung Horn Kramer & Woods

[57] ABSTRACT

A method of combating endoparasites which comprises applying thereto or to an endoparasite habitat an endoparasiticidally effective amount of an N-organooxycarbamic acid ester of the formula

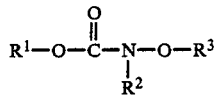

in which
R¹ represents alkyl, cycloalkyl, alkenyl, alkinyl or aryl, which can optionally be substituted,
R² represents alkyl, alkenyl or alkinyl, which can optionally be substituted, and
R³ represents alkyl, alkenyl or alkinyl, which can optionally be substituted.

Those compounds wherein one of R² and R³ is alkinyl are new.

8 Claims, No Drawings

N-ORGANOOXYCARBAMIC ACID ESTERS FOR COMBATING ENDOPARASITES

The present invention relates to the use of new N-organooxycarbamic acid esters for combating endoparasites, new N-organooxycarbamic acid esters and processes for their preparation.

N-Organocarbamic acid esters are already known. However, nothing is known of their use against endoparasites.

Alkyl- and phenylcarbonyl-substituted hydroxylamines and their anthelmintic action are already known. However, their action is not satisfactory in all cases.

1. It has been found that N-organooxycarbamic acid esters of the formula I

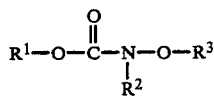

in which
  $R^1$ represents alkyl, cycloalkyl, alkenyl, alkinyl or aryl, which can optionally be substituted,
  $R^2$ represents alkyl, alkenyl or alkinyl, which can optionally be substituted, and
  $R^3$ represents alkyl, alkenyl or alkinyl, which can optionally be substituted,
are suitable for combating endoparasites in medicine and veterinary medicine.

The compounds of the formula I are known in some cases and can be prepared by processes analogous to known processes.

2. New N-organooxycarbamic acid esters of the formula

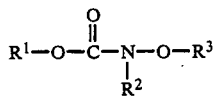

in which
  $R^1$ represents alkyl, cycloalkyl, alkenyl, alkinyl or aryl, which are optionally substituted,
  $R^2$ represents alkyl, alkenyl or alkinyl, which are optionally substituted, and
  $R^3$ represents alkyl, alkenyl or alkinyl, which are optionally substituted,
with the proviso that at least one of the radicals $R^2$ or $R^3$ represents alkinyl, preferably propargyl, have been found, 3. N-Organooxycarbamic acid esters of the formula I

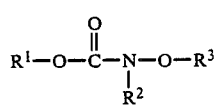

in which
  $R^1$ represents alkyl, cycloalkyl, alkenyl, alkinyl or aryl, which are optionally substituted,
  $R^2$ represents alkyl, alkenyl or alkinyl, which are optionally substituted, and
  $R^3$ represents alkyl, alkenyl or alkinyl, which are optionally substituted,
with the proviso that at least one of the radicals $R^2$ or $R^3$ represents propargyl, are prepared by a process in which
  (a) hydroxylamine derivatives of the formula II

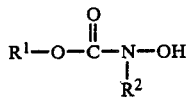

in which
  $R^1$ and $R^2$ have the abovementioned meaning, are reacted with compounds of the formula III

in which
  $R^3$ has the abovementioned meaning and
  X represents halogen or p-tolylsulphonyl, in the presence of bases, or
  (b) carbonic acid esters of the formula IV

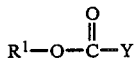

in which
  $R^1$ has the abovementioned meaning and
  Y represents halogen, azido or the radical —O—$R^1$,
are reacted with hydroxylamine derivatives of the formula V or their salts with acids,

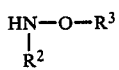

in which
  $R^2$ and $R^3$ have the abovementioned meaning, in the presence of bases, or
  (c) hydroxylamine derivatives of the formula VI

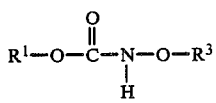

in which
  $R^1$ and $R^3$ have the abovementioned meaning, are reacted with compounds of the formula VII

in which
  X and $R^2$ have the abovementioned meaning, in the presence of bases, or
  (d) carbamic acid halides of the formula VIII

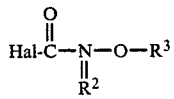

in which
  Hal represents halogen and
  $R^2$ and $R^3$ have the abovementioned meaning, are reacted with compounds of the formula IX

in which
R$^1$ has the abovementioned meaning, in the presence of bases.

The compounds of the formula I are outstandingly suitable for combating endoparasites, in particular in the field of veterinary medicine. In addition, they can also be used as insecticides, fungicides and herbicides in the fields of agriculture and forestry, in the domestic and hygiene fields and in the field of the preservation of stored products and materials.

Preferred compounds of the formula I are those in which

R$^1$ represents C$_{1-20}$-alkyl, C$_{2-20}$-alkenyl, C$_{3-20}$-cycloalkyl, C$_{2-20}$-alkinyl, phenyl or naphthyl, it being possible for these radicals to be substituted by one or more of the following substituents: alkyl with preferably 1 to 4, in particular 1 or 2, carbon atoms, such as methyl, ethyl, n.- and i.-propyl and n.-, i.-, s.- and t.-butyl; alkoxy with preferably 1 to 4, in particular 1 or 2, carbon atoms, such as methoxy, ethoxy, n.- and i.-propyloxy and n.-, i.-, s.- and t.-butyloxy; alkylthio with preferably 1 to 4, in particular 1 or 2, carbon atoms, such as methylthio, ethylthio, n.- and i.-propylthio and n.-, i.-, s.- and t.-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl and fluoro- and chloro-ethyl; halogenoalkoxy with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine such as trifluoromethoxy; halogenoalkylthio with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethylthio; in the case of phenyl, for alkylenedioxy with preferably 1 or 2 carbon atoms, such as methylenedioxy or ethylenedioxy; and in the case of phenyl, for halogen-substituted alkylenedioxy with preferably 1 or 2 carbon atoms and preferably 1 to 4, in particular 2 or 3, halogen atoms, the halogen atoms being identical or different and halogen atoms preferably being fluorine or chlorine, in particular fluorine, such as difluoromethylenedioxy, trifluoroethylenedioxy and tetrafluoroethylenedioxy. Other substituents are halogen, preferably fluorine, chlorine, bromine and iodine; in particular chlorine and bromine; cyano; nitro; dialkylamino with preferably 1 to 4, in particular 1 or 2, carbon atoms per alkyl group, such as dimethylamino, diethylamino and methyl-n.-butylamino; alkylcarbonyl with preferably 2-4 carbon atoms; carbalkoxy with preferably 2 to 4, in particular 2 or 3, carbon atoms, such as carbomethoxy and carbethoxy; alkylsulphonyl with preferably 1 to 4, in particular 1 or 2, carbon atoms, such as methylsulphonyl and ethylsulponyl; arylsulphonyl with preferably 6 or 10 aryl carbon atoms, such as phenylsulphonyl; phenyl, naphthyl, phenoxy, naphthoxy, phenylthio and naphthylthio, which can in turn be further substituted. R$^2$ represents C$_{1-6}$-alkyl, C$_{2-6}$-alkenyl or C$_{2-6}$-alkinyl, which can optionally be substituted by halogen, in particular chlorine, fluorine or bromine, and R$^3$ represents C$_{1-6}$-alkyl, C$_{2-6}$-alkenyl or C$_{2-6}$-alkinyl, which can optionally be substituted by halogen, in particular chlorine, fluorine or bromine.

Particularly preferred compounds of the formula I are those in which

R$^1$ represents C$_{1-4}$-alkyl which is optionally substituted by halogen, in particular chlorine or fluorine, C$_{1-4}$-alkoxy, such as methoxy or ethoxy, C$_{1-4}$-halogenoalkoxy, such as trifluoromethoxy, C$_{1-4}$-halogenoalkylthio, such as trifluoromethylthio, or phenyl, which is optionally substituted, or furthermore represents phenyl, which is optionally substituted by C$_1$-C$_4$-alkyl, in particular methyl, C$_1$-C$_4$-alkoxy, in particular methoxy or ethoxy, C$_1$-C$_4$-halogenoalkoxy, in particular trifluoromethoxy or fluorochloroethoxy, C$_1$-C$_4$-halogenoalkylthio, in particular trifluoromethylthio or fluorochloromethylthio, C$_1$-C$_4$-alkylthio, in particular methylthio, halogenosulphonyl, in particular fluorosulphonyl or chlorosulphonyl, C$_1$-C$_4$-alkylsulphonyl, in particular methylsulphonyl, C$_1$-C$_4$-halogenoalkylsulphonyl, in particular trifluoromethylsulphonyl, C$_1$-C$_4$-halogenoalkyl, in particular trifluoromethyl, methylenedioxy or ethylenedioxy, which are optionally substituted by fluorine or chlorine, halogen, in particular fluorine or chlorine, NO$_2$ or phenoxy, which is optionally substituted by one of the abovementioned radicals, R$^2$ represents C$_1$-alkyl, in particular methyl, ethyl, n-propyl, i-propyl or t-butyl, C$_{2-4}$-alkenyl, in particular allyl, chloropropenyl, dichloropropenyl or butenyl, or C$_{2-4}$-alkinyl, in particular propargyl, and R$^3$ independently of R$^2$ represents the radicals mentioned for R$^2$.

Especially preferred compounds of the formula I are those in which

R$^1$ represents C$_{1-4}$-alkyl, in particular methyl or ethyl, benzyl or phenyl, which is optionally substituted by halogen, in particular fluorine or chlorine, NO$_2$, CF$_3$, OCF$_3$, SCF$_3$, SCF$_2$CL, OCH$_3$, OCF$_2$CF$_2$H, —OCF$_2$CHFO—, —O—CH$_2$—O or —O—CF$_2$—O—, R$^2$ represents methyl, ethyl, n-propyl, i-propyl, butyl, pentyl, allyl, 3-chloro-prop-2-enyl, 2-chloro-prop-2-enyl, 3,3-dichloroprop-2-enyl, but-2-enyl or propargyl and R$^3$ independently of R$^2$ represents the radicals mentioned for R$^2$.

The following compounds of the formula I may be mentioned specifically:

| R$^1$ | R$^2$ | R$^3$ |
|---|---|---|
| C$_2$H$_5$ | CH$_3$— | —CH$_2$—CH=CH$_2$ |
| C$_2$H$_5$ | C$_2$H$_5$— | —CH$_2$—CH=CH$_2$ |
| C$_2$H$_5$ | C$_3$H$_7$— | —CH$_2$—CH=CH$_2$ |
| C$_2$H$_5$ | iC$_3$H$_7$— | —CH$_2$—CH=CH$_2$ |
| C$_2$H$_5$ | —CH$_2$—CH=CH$_2$ | —CH$_2$—CH=CH$_2$ |
| C$_2$H$_5$ | —CH$_2$—CH=CHCl | —CH$_2$—CH=CH$_2$ |
| C$_2$H$_5$ | —CH$_2$—C≡CH | —CH$_2$—CH=CH$_2$ |
| C$_2$H$_5$ | —CH$_2$—CH=CH—CH$_3$ | —CH$_2$—CH=CH$_2$ |
| C$_2$H$_5$ | —CH$_2$—CH=CH$_2$ | —CH$_2$—CH=CH$_2$ |
| CH$_3$— | CH$_3$— | —CH$_2$—CH=CH$_2$ |
| CH$_3$— | C$_2$H$_5$ | —CH$_2$—CH=CH$_2$ |
| CH$_3$— | iC$_3$H$_7$— | —CH$_2$—CH=CH$_2$ |
| CH$_3$— | —CH$_2$—CH=CH$_2$ | —CH$_2$—CH=CH$_2$ |

-continued

| R¹ | R² | R³ |
|---|---|---|
| CH₃— | —CH₂—C≡CH | —CH₂—CH=CH₂ |
| C₆H₅— | CH₃— | —CH₂—CH=CH₂ |
| C₆H₅— | C₂H₅— | —CH₂—CH=CH₂ |
| C₆H₅— | iC₃H₇— | —CH₂—CH=CH₂ |
| C₆H₅— | nC₃H₇— | —CH₂—CH=CH₂ |
| C₆H₅— | —CH₂—CH=CH₂ | —CH₂—CH=CH₂ |
| C₆H₅— | —CH₂—CH=CHCl | —CH₂—CH=CH₂ |
| C₆H₅— | —CH₂—C≡CH | —CH₂—CH=CH₂ |
| C₆H₅— | —CH₂—CH=CH—CH₃ | —CH₂—CH=CH₂ |
| C₂H₅— | CH₃— | —CH₂—C≡CH |
| C₂H₅— | iC₃H₇— | —CH₂—C≡CH |
| C₂H₅— | —CH₂—CH=CH₂ | —CH₂—C≡CH |
| C₂H₅— | —CH₂—C≡CH | —CH₂—C≡CH |
| C₂H₅— | —CH₂—CH=CHCl | —CH₂—C≡CH |
| C₂H₅— | —CH₂—CH=CCl₂ | —CH₂—C≡CH |
| C₂H₅— | —CH₂—CBr=CHBr | —CH₂—C≡CH |
| C₂H₅— | C₂H₅— | —CH₂—C≡CH |
| CH₃— | C₂H₅— | —CH₂—C≡CH |
| CH₃— | —CH₂—CH=CH₂ | —CH₂—C≡CH |
| CH₃— | —CH₂—CH=CHCl | —CH₂—C≡CH |
| CH₃— | —CH₂—C≡CH | —CH₂—C≡CH |
| CH₃— | —CH₂—CH=CH—CH₃ | —CH₂—C≡CH |
| C₆H₅— | CH₃— | —CH₂—C≡CH |
| C₆H₅— | C₂H₅— | —CH₂—C≡CH |
| C₆H₅— | —CH₂—CH=CH₂ | —CH₂—CH≡CH |
| C₆H₅— | —CH₂—C≡CH | —CH₂—C≡CH |
| C₆H₅— | —CH₂—CH=CHCl | —CH₂—C≡CH |

If benzyloxycarbonyl-N-propargylhydroxylamine is used as the hydroxylamine derivative of the formula II and allylbromide is used as the compound of the formula III in process 3a, the course of the reaction can be represented by the following equation:

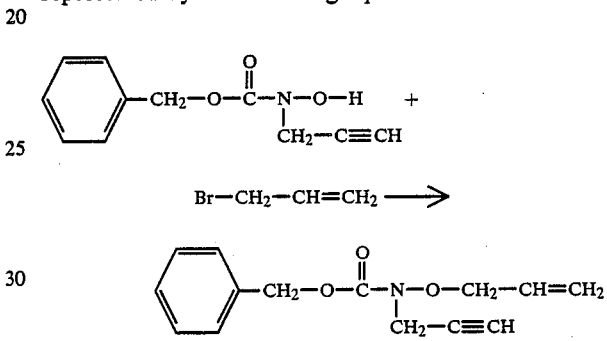

Compounds of the formulae II and III in which R¹, R² and R³ have the meanings given as preferred and particularly preferred in the case of the compounds of the formula and X represents chlorine, bromine or p-tolylsulphonyl are preferably used.

The following compounds of the formula II may be mentioned specifically: ethyl N-hydroxy-N-methyl-carbamate, methyl N-hydroxy-N-methyl-carbamate, ethyl N-hydroxy-N-allyl-carbamate, methyl N-hydroxy-N-propargyl-carbamate, phenyl N-hydroxy-N-ethyl-carbamate, ethyl N-hydroxy-N-3-chloroallyl-carbamate, isopropyl N-hydroxy-N-crotyl-carbamate, phenyl N-hydroxy-N-propargyl-carbamate, p-chlorophenyl N-hydroxy-N-allyl-carbamate, cyclopropyl N-hydroxy-N-propargyl-carbamate.

The compounds of the formula II are known or can be prepared by processes which are analogous to known processes (Houben-Weyl, volume E4, page 255, Stuttgart 1983).

The following compounds of the formula III may be mentioned specifically: methyl, ethyl, propyl, i-propyl, n-butyl, s-butyl, allyl, crotyl, 3-chloroallyl, 3,3-dichloroallyl, 2,3-dibromoallyl, propargyl and 2-butinyl chloride, bromide or tosylate.

The compounds of the formula III are known or can be prepared by processes analogous to known processes.

The reaction is carried out at temperatures of 0°–200° C., preferably at 20°–100° C. and particularly preferably at the boiling point of the diluent.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-di-chlorobenzene, and furthermore alcohols, such as methanol, ethanol, isopropanol and butanol, and furthermore ethers, such as diethyl ether, dibutyl ether, glycol dimethyl ether, diglycol dimethyl ether, tetrahydrofuran and dioxane, and furthermore ketones, such as acetone, methyl ethyl ketone, methyl isopropyl ketone and methyl isobutyl ketone, and also esters, such as methyl and ethyl acetate, and moreover nitriles, such as, for example, acetonitrile, propionitrile, benzonitrile and glutaric acid dinitrile, and in addition amides, such as, for example, dimethylformamide, dimethylacetamide and N-methylpyrrolidone, as well as dimethylsulphoxide, tetramethylene sulphone and hexamethylphosphoric acid triamide.

Possible bases are inorganic and organic bases. Bases which may be mentioned are alkali metal and alkaline earth metal hydroxides, carbonates, bicarbonates and alcoholates, and furthermore amines, such as, in particular, tertiary amines, for example trimethylamine, triethylamine, N-methylmorpholine, pyridine, picolines, N-ethylpyrrolidine, diazabicyclo(4,3,0)-undecane (DBU), 1,4-diazabicyclo(2,2,2)-octane (DABCO) and diazabicyclo(3,2,0)nonene (DBN).

The compounds of the formulae II and III are employed in an approximately equimolar ratio to one another. An excess of one either of the components provides no substantial advantage.

When the reaction has ended, the diluent is distilled off and the compounds of the formula I are isolated in a manner which is known per se, for example by extracting them from the residue with a suitable solvent, for example ether. The compounds of the formula I can be purified in the customary manner, for example by distillation.

If ethyl chloroformate is used as the carbonic acid ester of the formula IV and N-allyl-O-propargylhydroxylamine is used as the hydroxylamine derivative of the formula V in process 3b, the course of the reaction can be represented by the following equation:

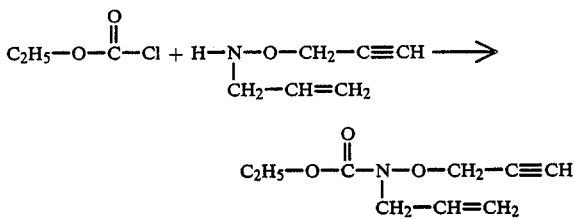

Compounds of the formula IV and V in which $R^1$, $R^2$ and $R^3$ have the meanings given as preferred and particularly preferred in the case of the compounds of the formula I and Y represents chlorine are preferably used. The compounds of the formula IV and V are known or can be prepared by processes analogous to known processes (European Offenlegungsschrift (European Published Specification No.) 29,171).

The following compounds of the formula IV may be mentioned specifically: methyl chloroformate, ethyl chloroformate, n-propyl chloroformate, isopropyl chloroformate, cyclopropyl chloroformate, benzyl chloroformate, phenyl chloroformate, p-chlorophenyl chloroformate, p-nitrophenyl chloroformate and p-tolyl chloroformate.

The following compounds of the formula V may be mentioned specifically: O,N-diallylhydroxylamine, O,N-dipropargylhydroxylamine, O-ethyl-N-allylhydroxylamine, O-methyl-N-propargyl-hydroxylamine, O-propargyl-N-ethylhydroxylamine, O-allyl-N-methylhydroxylamine, O-allyl-N-propargylhydroxylamine, O-crotyl-N-i-propylhydroxylamine, O-3-chloroally-N-propargylhydroxylamine, O-3,3-dichloroallyl-N-allylhydroxylamine, O-benzyl-N-3-chloroallylhydroxylamine and O-methyl-N-2-butinylhydroxylamine.

The hydroxylamines of the formula V can be used in the form of their salts with acids, for example as hydrochlorides.

The reaction is carried out at temperatures of $-50°$–$50°$ C., preferably at $0°$ C.–$30°$ C. and particularly preferably at room temperature.

Possible diluents are water and all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore alcohols, such as methanol, ethanol, isopropanol and butanol, and furthermore ethers, such as diethyl ether, dibutyl ether, glycol dimethyl ether, diglycol dimethyl ether, tetrahydrofuran and dioxan, and furthermore ketones, such as acetone, methyl ethyl ketone, methyl isopropyl ketone and methyl isobutyl ketone, and also esters, such as methyl and ethyl acetate, and moreover nitriles, such as, for example, acetonitrile, propionitrile, benzonitrile and glutaric acid dinitrile, and in addition amides, such as, for example, dimethylformamide, dimethylacetamide and N-methylpyrrolidone, as well as dimethyl sulphoxide, tetramethylene sulphone and hexamethylphosphoric acid triamide.

Possible bases are inorganic and organic bases. Bases which may be mentioned are alkali metal and alkaline earth metal hydroxides, carbonates, bicarbonates and alcoholates, and furthermore amines, such as, in particular, tertiary amines, for example trimethylamine, triethylamine, N-methylmorpholine, pyridine, picolines, N-ethylpyrrolidine, diazabicyclo(4,3,0)-undecane (DBU), 1,4-diazabicyclo(2,2,2)-octane (DABCO) and diazabicyclo(3,2,0)nonene (DBN).

The compounds of the formulae IV and V are employed in an approximately equimolar ratio to one another. An excess of either of the components provides no substantial advantage.

The reaction is preferably carried out in an aqueous solution of the hydrochlorides of the hydroxylamine derivatives of the formula V with carbonic acid esters of the formula IV in the presence of aqueous organic bases, such as potassium hydroxide or carbonate or sodium hydroxide or carbonate. When the reaction has ended, the compound I is isolated in a manner which is known per se, for example by extraction with a suitable solvent. The extract is washed several times with water, for example, dried over sodium sulphate and then freed from the solvent. The compounds of the formula I can then be purified in the customary manner, for example by distillation.

If benzyl N-propargyloxy-carbamate is used as the hydroxylamine derivative of the formula VI and 1,5-dibromopentane is used as the compound of the formula VIII in process 3c, the course of the reaction can be represented by the following equation:

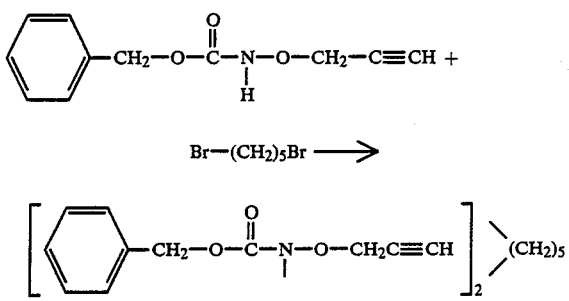

Compounds of the formula VI and VII in which $R^1$, $R^2$ and $R^3$ have the meanings given as preferred and particularly preferred in the case of the compounds of the formula I and X represents chlorine, bromine or p-tolylsulphonyl are preferably used. The compounds of the formulae VI and VII are known or can be prepared by processes which are analogous to known processes (Houben-Weyl, volume E4, page 258, Stuttgart, 1983).

The following compounds of the formula VI may be mentioned specifically: ethyl N-ethoxy-carbamate, ethyl N-allyloxycarbamate, ethyl N-proparyloxycarbamate, methyl N-crotyloxycarbamate, methyl N-(3-chloroallyloxy)-carbamate, phenyl N-propargyloxycarbamate, perchlorophenyl N-allyloxycarbamate and phenyl N-2-butinyloxycarbamate.

The following compounds of the formula VII may be mentioned specifically: methyl, ethyl, n-propyl, i-propyl, n-butyl, i-butyl, n-hexyl, allyl, crotyl, 3-chloroallyl, 3,3-dichloroallyl, 2,3-dibromoallyl, propargyl and 2-butinyl chloride, bromide or tosylate.

In the case where compounds of the formula I in which $R^2$ represents methyl or ethyl are to be prepared, dimethyl sulphate or diethyl sulphate can also be employed as the compounds of the formula VII.

The reaction is carried out at temperatures of 0°–200° C., preferably at 20°–130° C. and particularly preferably at the boiling point of the diluent.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore alcohols, such as methanol, ethanol, isopropanol and butanol, and furthermore ethers, such as diethyl ether, dibutyl ether, glycol dimethyl ether, diglycol dimethyl ether, tetrahydrofuran and dioxane, and furthermore ketones, such as acetone, methyl ethyl ketone, methyl isopropyl ketone and methyl isobutyl ketone, and also esters, such as methyl and ethyl acetate, and moreover nitriles, such as, for example, acetonitrile, propionitrile, benzonitrile and glutaric acid dinitrile, and in addition amides, such as, for example, dimethylformamide, dimethylacetamide and N-methylpyrrolidone, as well as dimethyl sulphoxide, tetramethylene sulphone and hexamethylphosphoric acid triamide.

Possible bases are inorganic and organic bases. Bases which may be mentioned are alkali metal and alkaline earth metal hydroxides, carbonates, bicarbonates and alcoholates, and furthermore amines, such as, in particular, tertiary amines, for example trimethylamine, triethylamine, N-methylmorpholine, pyridine, picolines, N-ethylpyrrolidine, diazabicyclo(4,3,0)-undecane (DBU), 1,4-diazabicyclo(2,2,2)-octane (DABCO) and diazabicyclo(3,2,0)nonene (DBN).

The compounds of the formulae VI and VII are employed in an approximately equimolar ratio to one another. An excess of either of the components provides no substantial advantage.

When the reaction has ended, the diluent is distilled off and the compounds of the formula I are isolated in a manner which is known per se, for example by extracting them from the residue with a suitable solvent, for example ether. The compounds of the formula I can be purified in the customary manner, for example by distillation.

If N-(2-butenoxy)-N-propargylcarbamoyl chloride is used as the carbamic acid halide of the formula VIII and phenol is used as the compound of the formula IX in process 3d, the reaction mechanism can be represented by the following equation:

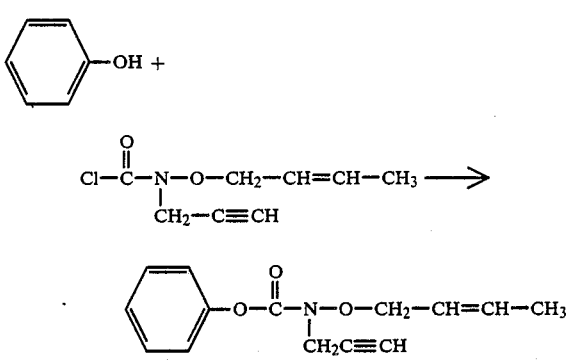

Compounds of the formula VIII and IX in which $R^1$, $R^2$ and $R^3$ have the meanings given as preferred and particularly preferred in the case of the compounds of the formula I and Hal represents chlorine or bromine are preferably used.

The compounds of the formulae VIII and IX are known or can be prepared by processes analogous to known processes. (Houben-Weyl, volume E4, Stuttgart 1983, page 258).

The following compounds of the formula VIII may be mentioned specifically: N-methoxy-N-allyl-carbamoyl chloride, N-allyloxy-allylcarbamoyl chloride, N-ethoxy-N-propargylcarbamoyl chloride, N-allyloxy-N-propargyl-carbamoyl chloride, N-propargyloxy-N-ethyl-carbamoyl chloride, N-benzyloxy-N-propargyl-carbamoyl chloride and N-propargyloxy-N-propargyl-carbamoyl chloride.

The following compounds of the formula IX may be mentioned specifically: methanol, ethanol, propanol, isopropanol, n-, i-, s- and t-butanol, pentanols, hexanol, cyclohexanol, allyl alcohol, propargyl alcohol, phenol, p-cresol, p-chlorophenol, α-naphthol and p-nitrochlorophenol.

The reaction is carried out at temperatures of −50°–50° C., preferably at 0° C.–30° C. and particularly preferably at room temperature.

Possible diluents are water and all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-di-chlorobenzene, and furthermore alcohols, such as methanol, ethanol, isopropanol and butanol, and furthermore ethers, such as diethyl ether, dibutyl ether, glycol dimethyl ether, diglycol dimethyl ether, tetrahydrofuran and dioxane, and furthermore ketones, such as acetone, methyl ethyl ketone, methyl isopropyl ketone and methyl isobutyl ketone, and also esters, such as methyl and ethyl acetate, and moreover nitriles, such as, for example, acetonitrile, propionitrile, benzonitrile and glutaric acid dinitrile, and in addition amides, such as, for example, dimethylformamide, dimethylacetamide and N-methylpyrrolidone, as well as dimethylsulphoxide, tetramethylene sulphone and hexamethylphosphoric acid triamide.

Possible bases are inorganic and organic bases. Bases which may be mentioned are alkali metal and alkaline earth metal hydroxides, carbonates, bicarbonates and alcoholates, and furthermore amines, such as, in particular, tertiary amines, for example trimethylamine, triethylamine, N-methylmorpholine, pyridine, picolines, N-ethylpyrrolidine, diazabicyclo(4,3,0)-undecane (DBU), 1,4-diazabicyclo(2,2,2)-octane (DABCO) and diazabicyclo(3,2,0)nonene (DBN).

The compounds of the formulae VIII and IX are employed in an approximately equimolar ratio to one another. An excess of either of the components provides no substantial advantage.

When the reaction has ended, the compound I is isolated in a manner which is known per se, for example by extraction with a suitable solvent. The extract is washed several times with water, for example, dried over sodium sulphate and then freed from the solvent. The compounds of the formula I can then be purified in the customary manner, for example by distillation.

The active compounds have a favourable toxicity towards warm-blooded animals and are suitable for combating pathogenic endoparasites which occur in humans and in animal husbandry and animal breeding in useful, stock, zoo, laboratory and experimental animals and pets. They are effective against all or individual development stages of the pests and against resistant and normally sensitive species. By combating the pathogenic endoparasites, disease, fatalities and reductions in yield (for example in the production of meat, milk, wool, skins, eggs, honey and the like) are said to be reduced, so that more economical and easier animal husbandry is possible by using the active substances. The pathogenic endoparasites include cestodes, trematodes, nematodes and Acanthocephalas, in particular:

From the order of the Pseudophyllidea for example: Diphyllobothrium spp., Spirometra spp., Schistocephalus spp., Ligula spp., Bothridium spp., Diphlogonoporus spp..

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the sub-class of Monogenea, for example: Gyrodactylus spp., Dactylogyrus spp., Polystoma spp..

From the sub-class of Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp. and Metagonimus spp..

From the order of the Enoplida, for example: Trichuris spp., Capillaria spp., Trichomosoides spp. and Trichinella spp..

From the order of the Rhabditia, for example: Micronema spp., Strongyloides spp..

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp. and Ollulanus spp..

From the order of the Oxyurida, for example: Oxyuris spp., Enterobius spp., Passalurus spp., Syphacia spp., Aspiculuris spp. and Heterakis spp..

From the order of the Ascaridia, for example: Ascaris spp., Toxascaris spp., Toxocara spp., Parascaris spp., Anisakis spp. and Ascaridia spp..

From the order of the Spirurida, for example: Gnathostoma spp., Physaloptera spp., Thelazia spp., Gongylonema spp., Habronema spp., Parabronema spp., Draschia spp., Dracunculus spp..

From the order of the Filariida, for example: Stephanofilaria spp., Parafilaria spp., Setaria spp., Loa spp., Dirofilaria spp., Litomosoides spp., Brugia spp., Wuchereria spp. and Onchocerca spp..

From the order of the Gigantorhynchida, for example: Filicollis spp., Moniliformis spp., Macracanthorhynchus spp. and Prosthenorchis spp..

The useful and breeding animals include mammals, such as, for example, cattle, horses, sheep, pigs, goats, camels, water buffalo, donkeys, rabbits, fallow deer and reindeer, fur-bearing animals, such as, for example, mink, chinchillas and raccoons, birds, such as, for example, chicken, geese, turkeys and ducks, freshwater and salt water fish, such as, for example, trout, carp and eels, reptiles and insects, such as, for example, honey bees and silk worms.

The laboratory and experimental animals include mice, rats, guinea pigs, golden hamsters, dogs and cats.

The pets include dogs and cats.

The compounds can be used either prophylactically or therapeutically.

The active compounds are used directly or in the form of suitable formulations enterally, parenterally, dermally, nasally, by treatment of the environment or with the aid of shaped articles containing the active compound, such as, for example, strips, plates, tapes, collars, ear tags, limb bands or marking devices.

Enteral use of the active compounds is effected, for example, orally in the form of powders, tablets, capsules, pastes, drinks, granules, solutions, suspensions and emulsions for oral administration, boli or medicated feed or drinking water. Dermal use is effected, for example, in the form of dipping, spraying or pour-on and spot-on formulations. Parenteral use is effected, for example, in the form of an injection (intramuscular, subcutaneous, intravenous or intraperitoneal) or by implants.

Suitable formulations are: solutions, such as injection solutions, oral solutions, concentrates for oral administration after dilution, solutions for use on the skin or in body cavities, infusion formulations and gels; emulsions and suspensions for oral or dermal use and for injection; semi-solid formulations; formulations in which the active compound is worked into an ointment base or into an oil-in-water or water-in-oil emulsion base; solid formulations, such as powders, premixes or concentrates, granules, pellets, tablets, boli or capsules; aerosols and inhalates and shaped articles containing the active compound.

Injection solutions are administered intravenously, intramuscularly and subcutaneously.

Injection solutions are prepared by dissolving the active compound in a suitable solvent and adding any additives such as solubilizing agents, acids, bases, buffer salts, antioxidants and preservatives. The solutions are subjected to sterile filtration and bottled.

Solvents which may be mentioned are: physiologically acceptable solvents, such as water, alcohols, such as ethanol, butanol, benzyl alcohol, glycerol, propylene glycol and polyethylene glycols, N-methyl-pyrrolidone and mixtures thereof.

If appropriate, the active compounds can also be dissolved in physiologically acceptable vegetable or synthetic oils suitable for injection.

Solubilizing agents which may be mentioned are: solvents which promote solution of the active compound in the main solvent or prevent its precipitation. Examples are polyvinyl pyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are used directly. Concentrates are used orally after prior dilution to the use concentration. Oral solutions and concentrates are prepared as described above for the injection solutions, and sterile operation can be dispensed with.

Solutions for use on the skin are dripped on, brushed on, massaged in, sprinkled on or sprayed on. These solutions are prepared as described above for the injection solutions.

It may be advantageous to add thickeners during preparation. Thickeners are: inorganic thickeners, such as bentonites, colloidal silicic acid and aluminum monostearate, and organic thickeners, such as cellulose derivatives, polyvinyl alcohols and copolymers thereof, acrylates and metacrylates.

Gels are applied or brushed onto the skin or introduced into body cavities. Gels are prepared by adding an amount of thickeners to solutions which have been prepared as described for the injection solutions such that a clear composition with an ointment-like consistency is formed. The thickeners used are the thickeners mentioned above.

Pour-on formulations are poured or sprinkled onto limited areas of the skin, the active compound penetrating through the skin and having a systemic action.

Pour-on formulations are prepared by dissolving, suspending or emulsifying the active compound in suitable solvents or solvent mixtures which are tolerated by the skin. If appropriate, other additives, such as dyestuffs, substances which promote absorption, antioxidants, light stabilizers and adhesives, are added.

Solvents which may be mentioned are: water, alkanols, glycols, polyethylene glycols, polypropylene glycols, glycerol, aromatic alcohols, such as benzyl alcohol, phenylethanol and phenoxyethanol, esters, such as ethyl acetate, butyl acetate and benzyl benzoate, ethers, such as alkylene glycol alkyl ethers, such as dipropylene glycol monomethyl ether and diethylene glycol monobutyl ether, ketones, such as acetone and methyl ethyl ketone, aromatic and/or aliphatic hydrocarbons, vegetable or synthetic oils, dimethylformamide, dimethylacetamide, N-methylpyrrolidone and 2-dimethyl-4-oxymethylene-1,3-dioxolane.

Dyestuffs are all the dyestuffs permitted for use on animals, and they can be dissolved or suspended.

Examples of substances which promote absorption are dimethylsulphoxide, spreading oils, such as isopropyl myristate, dipropylene glycol pelargonate and silicone oils, fatty acid esters, triglycerides and fatty alcohols.

Antioxidants are sulphites or metabisulphites, such as potassium metabisulphite, ascorbic acid, butylhydroxytoluene, butylhydroxyanisole or tocopherol.

Light stabilizers are, for example, novantisolic acid.

Adhesives are, for example, cellulose derivatives, starch derivatives, polyacrylates, natural polymers, such as alginates, and gelatin.

Emulsions can be used orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and if appropriate other auxiliaries, such as dyestuffs, substances which promote absorption, preservatives, antioxidants, light stabilizers and substances which increase the viscosity.

Hydrophobic phases (oils) which may be mentioned are: paraffin oils, silicone oils, natural vegetable oils, such as sesame oil, almond oil and castor oil, synthetic triglycerides, such as caprylic/capric acid biglyceride, a triglyceride mixture with vegetable fatty acids of $C_{8-12}$ chain length or other specifically selected naturally occurring fatty acids, partial glyceride mixtures of saturated or unsaturated fatty acids, which may also contain hydroxyl groups, and mono- and diglycerides of $C_8/C_{10}$-fatty acids.

Fatty acid esters, such as ethylstearate, di-n-butyryl adipate, hexyl laurate and dipropylene glycol pelargonate, esters of a branched fatty acid of medium chain length with saturated fatty alcohols of $C_{16}$–$C_{18}$ chain length, isopropyl myristate, isopropyl palmitate, caprylic/capric acid esters of saturated fatty alcohols of $C_{12}$–$C_{18}$ chain length, isopropyl stearate, oleyl oleate, decyl oleate, ethyl oleate and ethyl lactate, waxy fatty acid esters, such as synthetic uropigeal gland fat, dibutyl phthalate and diisopropyl adipate, ester mixtures related to the latter and the like.

Fatty alcohols, such as isotridecyl alcohol, 2-octyldodecanol, cetyl stearyl alcohol and oleyl alcohol.

Fatty acids, such as, for example, oleic acid and their mixtures.

Hydrophilic bases which may be mentioned are: water, alcohols, such as, for example, propylene glycol, glycerol and sorbitol, and their mixtures.

Emulsifiers which may be mentioned are: nonionic surfactants, for example polyoxyethylated castor oil, polyoxyethylated sorbitan monooleate, sorbitan monostearate and glycerol monostearate, polyoxyethyl stearate and alkylphenyl polyglycol ethers; ampholytic surfactants, such as di-Na N-lauryl-β-iminodipropionate or lecithin; anionic surfactants, such as Na laurylsulphate, fatty alcohol ethersulphates and mono/dialkyl polyglycol ether-orthophosphoric acid ester monoethanolamine salt; and cationic surfactants, such as cetyltrimethylammonium chloride.

Further auxiliaries which may be mentioned are: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be used orally, dermally or as an injection. They are prepared by suspending the active compound in a suitable carrier liquid, if appropriate with the addition of other auxiliaries, such as wetting agents, dyestuffs, substances which promote absorption, preservatives, antioxidants and light stabilizers.

Carrier liquids which may be mentioned are all the homogeneous solvents and solvent mixtures.

Wetting agents (dispersing agents) which may be mentioned are the surfactants mentioned above.

Other auxiliaries which may be mentioned are those mentioned above.

Semi-solid formulations can be administered orally or dermally. They differ from the suspensions and emulsions described above only by their higher viscosity.

To prepare solid formulations, the active compound is mixed with suitable excipients, if appropriate with the addition of auxiliaries, and the mixture is brought into the desired shape.

Excipients which may be mentioned are all the physiologically acceptable solid inert substances. Substances which may be used all such are inorganic and organic substances. Inorganic substances are, for example, sodium chloride, carbonates, such as calcium carbonate, bicarbonates, aluminum oxides, silicic acids, aluminas, precipitated or colloidal silicon dioxide and phosphates.

Organic substances are, for example, sugars, cellulose, foodstuffs and feedstuffs, such as milk powder, animal flours, cereal flours and shredded cereals and starches.

Auxiliaries are preservatives, antioxidants and dyestuffs, which have already been listed above.

Other suitable auxiliaries are lubricants and slip agents, such as, for example, magnesium stearate, stearic acid, talc and bentonites, substances which promote disintegration, such as starch or crosslinked polyvinylpyrrolidone, binders, such as, for example, starch, gelatin or linear polyvinylpyrrolidone, and dry binders, such as microcrystalline cellulose.

The active compounds can also be present in the formulations as a mixture with synergists or with other active compounds which act against pathogenic endoparasites. Examples of such active compounds are L-2,3,5,6-tetrahydro-6-phenylimidazothiazole, benzimidazolecarbamates, praziquantel, pyrantel and febantel.

Ready-to-use formulations contain the active compound in concentrations of 10 ppm–20 per cent by weight, preferably 0.1–10 per cent by weight.

Formulations which are diluted before use contain the active compound in concentrations of 0.5–90 per cent by weight, preferably 5 to 50 per cent by weight.

In general, it has proved advantageous to administer amounts of about 1 to about 100 mg of active compound per kg of body weight per day to achieve effective results.

EXAMPLE A

In vivo nematode test

Ascarides/dog

Dogs naturally infected with *Toxascaris leonina* were treated. The active compounds were administered orally as the pure active compound in gelatin capsules.

The degree of action is determined by counting the number of worms excreted with the faeces. The number of worms which have not been killed and excreted by the treatment is then determined after autopsy of the dog.

| Active compound Example No. | Parasite | Effective dose (mg/kg) |
| --- | --- | --- |
| 3 | Toxascaris Leonina | 25 |

EXAMPLE B

In vivo nematode test

Hookworm/dog

Dogs infected experimentally with *Ancylostoma caninum* or *Unicinaria stenocephala* were treated after the prepatency period of the parasite had elapsed. The active compounds were administered orally as the pure active compound in gelatin capsules.

The degree of action is determined by counting the worms excreted with the faeces. The number of worms which have not been killed and excreted by the treatment is then determined after autopsy of the dogs.

| Active compound Example No. | Parasite | Effective dose (mg/kg) |
| --- | --- | --- |
| 3 | Ancylostoma caninum | 25 |
| 3 | Unicinaria stenocephala | 25 |

EXAMPLE C

In vivo nematode test

*Nippostronglyos brasiliensis*/rat

Rats experimentally infected with *Nippostrongylus brasiliensis* are treated orally by means of a stomach tube on three successive days 6 days after the infection. The animals are sacrificed 12 days after the infection and the number of parasites is determined. The active compound concentration at which at least 95% of the parasites have been killed (effective dose) is stated:

| Active compound Example No. | Effective dose mg/kg |
| --- | --- |
| 4 | 250 |
| 1 | 100 |
| 30 | 250 |
| 31 | 250 |
| 19 | 100 |
| 34 | 100 |
| 38 | 100 |
| 41 | 100 |
| 52 | 100 |

EXAMPLE D

In vivo nematode test

Haemonchus contortus/sheep

Sheep infected experimentally with *Haemonchus contortus* were treated after the prepatency period of the parasite had elapsed. The active compounds were administered orally as the pure active compound in gelatine capsules.

The degree of action is determined by quantitative counting of the worms excreted with the faeces before and after treatment.

A complete halt in the excretion of eggs after treatment means that the worms have been expelled or are so damaged that they can no longer produce eggs (effective dose).

The active compounds tested and the effective dosages can be seen from the following table:

| Active compound Example No. | Effective dose in mg/kg |
| --- | --- |
| 4 | 50 |
| 3 | 25 |
| 30 | 10 |
| 34 | 10 |
| 48 | 10 |
| 50 | 25 |
| 45 | 25 |
| 43 | 25 |
| 31 | 25 |

EXAMPLE E

In vivo nemetode test

*Trichostrongylus colubriformis*/Sheep

Sheep infected experimentally with *Trichostrongylus colubriformis* were treated after the prepatency period of the parasite had elapsed. The active compounds were administered orally as the pure active compound in gelatine capsules.

The degree of action is determined by quantitative counting of the worm eggs excreted with the faeces before and after treatment.

A complete halt in the excretion of eggs after treatment means that the worms have been expelled or are so damaged that they can no longer produce eggs (effective dose).

The active compounds tested and the effective dosages can be seen from the following table:

| Active compound | Effective dose in mg/kg |
| --- | --- |
| 1 | 10 |
| 3 | 5 |
| 30 | 2.5 |
| 41 | 5 |
| 26 | 5 |
| 14 | 10 |
| 21 | 10 |
| 22 | 10 |
| 44 | 10 |

EXAMPLE F

In vivo trematode test

*Fasciola hepatica*/rat

Rats experimentally infected with Metacercaria of *Fasciola hepatica* were treated orally by means of a stomach tube on three successive days after the infection. The animals were sacrificed 2 weeks after the infection and the number of juvenile liver fluke in the liver parenchyma is determined.

The dose (effective dose) necessary to achieve a 95% reduction in parasites in comparison with an untreated control is given in the following table.

| Active compound Example No. | Effective dose ED95 (mg/kg × 3) |
| --- | --- |
| 1 | 25 |
| 3 | 10 |
| 4 | 100 |
| 9 | 250 |
| 14 | 50 |
| 30 | 25 |
| 21 | 50 |
| 22 | 25 |
| 31 | 50 |
| 19 | 10 |
| 34 | 25 |
| 38 | 25 |
| 44 | 50 |

PREPARATION EXAMPLES (a) General instructions for the preparation of the N-organooxycarbamic acid esters of the formula I: according to process 3(a)

0.1 mol of the N-alkyl-N-hydroxy-carbamic acid ester of the formula II and 0.1 mol of the alkylating agent of the formula III are introduced into a solution of 6 g of potassium hydroxide in 30 ml of ethanol and the mixture is boiled under reflux for 5 hours. The alcohol is distilled off and the crude ester is extracted with ether. After evaporation of the ether, the residue is distilled in vacuo.

(b) General instructions according to process 3(b)

0.1 mol of the N,O-dialkylhydroxylamine hydrochloride of the formula (V), 25 ml of water and 100 ml of ether are taken and 0.2 mol of sodium bicarbonate is added at room temperature, with vigorous stirring. The mixture is subsequently stirred at room temperature for 40 minutes and then cooled to 0° C., and 0.1 mol of the chloroformic acid ester of the formula VI is added dropwise. The mixture is then subsequently stirred at room temperature for 24 hours and the ether phase is separated off, dried over Na$_2$SO$_4$ and concentrated. The residue is analyzed (gas chromatography) and if appropriate distilled in vacuo.

(c) General instructions according to process 3(c)

0.1 mol of the N-alkoxycarbamic acid ester of the formula VI and 0.1 mol of sodium hydroxide solution are taken in 100 ml of methanol and 10 ml of water, and 0.1 mol of the alkylating reagent of the formula VII is added at room temperature. The mixture is subsequently stirred at room temperature for 48 hours, the alcohol is evaporated off and the residue is extracted with ether. The ether extracts are dried, the ether is distilled off and the residue is distilled.

The active compounds of the following examples are obtained analogously to processes 3c:

Examples $$R^1-O-\underset{\underset{O}{\|}}{C}-\underset{\underset{R^2}{|}}{N}-O-R^3$$

| Ex. | $R^1$ | $R^2$ | $R^3$ | $^1$H-NMR Data (ppm) |
|---|---|---|---|---|
| 1 | $C_2H_5-$ | $CH\equiv C-CH_2-$ | $CH_2=CH-CH_2-$ | 1.32 (t,3H), 2.27 (t,1H) 4.23 (m,4H) 4.48 (q,2H), 5.32 (m,2H), 6.0 (m,1H) |
| 2 | $C_2H_5-$ | $CH_2=CH-CH_2-$ | $CH\equiv C-CH_2-$ | 1.3 (t,3H), 2.51 (t,1H), 4.22 (m,4H) 4.52 (d,2H), 5.22 (m,2H), 5.9 (m,1H) |
| 3 | $C_2H_5-$ | $CH\equiv C-CH_2-$ | $CH\equiv C-CH_2-$ | 1.32 (t,3H), 2.29 (t,1H), 2.55 (t,1H) 4.27 (q,2H), 4.35 (d,2H), 4.59 (d,2H) |
| 4 | $C_2H_5-$ | $CH_2=CH-CH_2-$ | $CH_2=CH-CH_2-$ | 1.32 (t,3H), 4.09 (d,2H), 4.22 (q,2H) 4.38 (d,2H), 5.25 (m, YH), 5.92 (m,2H) |
| 5 | $C_2H_5-$ | $CH_3-$ | $CH_2=CH-CH_2-$ | 1.32 (t,3H), 3.18 (s,3H), 4.2 (q,2H) 4.35 (d,2H), 5.3 (m,2H), 6.0 (m,1H) |
| 6 | $C_2H_5-$ | $CH_3-CH=CH-CH_2-$ | $CH_2=CH-CH_2$ | 1.3 (t,3H), 1.7 (d,3H), 4.0 (d,2H), 4.21 (q,2H), 4.35 (d,2H) 5.29 (m,2H) 5.5 (m,1H), 5.69 (m,1H), 5.98 (m,1H) |
| 7 | $C_2H_5-$ | $C_2H_5-$ | $CH_2=CH-CH_2-$ | 1.19 (t,3H), 1.32 (t,3H), 3.55 (q,2H) 4.22 (q,2H), 4.38 (d,2H), 5.29 (m,2H), 5.97 (m,1H) |
| 8 | $C_2H_5-$ | $CH_3-CH_2-CH_2-$ | $CH_2=CH-CH_2-$ | 0.92 (t,3H), 1.32 (t,3H), 1.67 (m,2H), 3.48 (t, 2H), 4.21 (q,2H), 4.38 (d,2H), 5.3 (m,2H), 5.98 (m,1H) |
| 9 | $C_6H_5-$ | $CH_2=CH-CH_2-$ | $CH_2=CH-CH_2-$ | 4.21 (q,2H), 4.41 (q,2H), 5.2–5.4 (m,4H), 5.88–6.08 (m,2H), 7.05–7.4 (m,5H) |
| 10 | $CH_3-$ | $C_2H_5-$ | $CH_2=CH-CH_2-$ | 1.08 (t,3H), 3.42 (q,2H), 3.65 (s,3H), 4.3 (q,2H), 5.22–5.37 (m, 2H), 5.95 (m,1H), |
| 11 | $CH_3-$ | $CH_3-$ | $CH\equiv C-CH_2-$ | 2.5 (t,1H), 3.23 (s,3H), 3.77 (s,3H), 4.5 (d,2H) |
| 12 | $CH_3-$ | $C_2H_5-$ | $CH\equiv C-CH_2-$ | 1.18 (t,3H), 2.52 (t,1H), 3.57 (q, 2H), 3.78 (s,3H), 4.5 (d,2H) |
| 13 | $CH_3-$ | $ClCH=CH-CH_2-$ | $CH\equiv C-CH_2-$ | |
| 14 | $CH_3-$ | $CH_2=CH-CH_2-$ | $CH\equiv C-CH_2-$ | 2.5 (t,1H), 3.75 (s,3H), 4.5 (d,2H), 5.2 (m,2H), 5.9 (m,1H) |
| 15 | $CH_3-$ | $CH_3-$ | $CH_2=CH-CH_2-$ | 3.15 (s,3H), 3.79 (s,3H), 4.3 (q,2H), 5.2–5.4 (m,2H), 5.95 (m,1H) |
| 16 | $CH_3-$ | $i-C_3H_7-$ | $CH_2=CH-CH_2-$ | 1.18 (d,2H), 3.75 (s,3H), 4.18–4.3 (m,1H), 4.38 (q,2H), 5.2–5.38 (m,2H), 5.95 (m,1H) |
| 17 | $C_2H_5-$ | $CH_3-CH=CH-CH_2-$ | $CH_3-CH=CH-CH-$ | |
| 18 | $CH_3-$ | $CH_3-CH=CH-CH_2-$ | $CH_3-CH=CH-CH_2-$ | |
| 19 | $CH_3-$ | $CH\equiv C-CH_2-$ | $CH_2=CH-CH_2-$ | |
| 20 | $C_2H_5-$ | $ClCH=CH-CH_2-$ | $ClCH=CH-CH_2-$ | 1.3 (m,3H), 4.0–4.65 (m,6H), 6.0 (m,2H), 6.28 (m,2H) |
| 21 | $C_2H_5-$ | $CH\equiv C-CH_2-$ | $ClCH=CH-CH_2-$ | 1.3 (t,3H), 2.28 (t,1H), 4.28 (m,2H), 4.45 (d,2H), 4.7 (d,2H), 6.1 (m,1H), 6.28 (m,1H) |
| 22 | $C_2H_5-$ | $CH_2=CH-CH_2-$ | $ClCH=CH-CH_2-$ | 1.3 (t,3H), 4.1 (m,2H), 4.22 (m,2H), 4.35 (d,14), 4.61 (d,1H), 5.25 (m,2H), 5.4 (m,1H), 6.05 (m,1H), 6.25 (m,1H), 5.9 (m,1H) |
| 23 | $C_2H_5-$ | $ClCH=CH-CH_2-$ | $CH\equiv C-Ch_2-$ | 1.3 (t,3H), 2.55 (t,1H), 4.15 (d,1H), 4.2 (q,2H), 4.4 (d,1H), 4.5 (m,2H), 5.9–6.2 (2H) |
| 24 | $C_2H_5-$ | $ClCH=CH-CH_2-$ | $CH_2=CH-CH_2-$ | 1.3 (t,3H), 4.1–4.4 (m,6H), 5.3 (m,3H), 5.95 (m,2H), 6.2 (m,1H) |
| 25 | $CH_3-$ | $CH_2=CH-CH_2-$ | $CH_2=CH-CH_2-$ | 3.78 (s,3H), 4.1 (d,2H), 4.38 (d,2H), 5.25 (m,4h), 5.9 (m,2H) |
| 26 | $CH_3-$ | $CH\equiv C-CH_2-$ | $CH\equiv C-CH_2-$ | 2.3 (t,1H), 2.52 (t,1H), 3.82 (s,3H), 4.35 (d,2H), 4.59 (d,2H) |
| 27 | $C_2H_5-$ | $CH_3-$ | $CH\equiv C-CH_2-$ | 1.32 (t,3H), 2.5 (t,1H), 3.25 (s, 3H), 4.22 (q,2H), 4.5 (d,2H) |
| 28 | $C_2H_5-$ | $i-C_3H_7-$ | $CH\equiv C-CH_2-$ | 1.22 (d,6H), 1.31 (t,3H), 2.5 (t,1H), 3.8 (sept,1H), 4.2 (q,2H), 4.5 (d,2H) |
| 29 | $C_2H_5-$ | $C_2H_5-$ | $CH\equiv C-CH_2-$ | 1.1 (t,3H), 1.3 (t,3H), 2.5 (t,1H), 4.2–4.4 (2q,4H), 4.5 (d,2H) |
| 30 | $C_2H_5-$ | $-CH_2-C\equiv CH$ | $-C_2H_5$ | 2.3 (t,1H), $\equiv$CH) |
| 31 | $C_2H_5-$ | $-CH_2-CH=CH_2$ | $-C_2H_5$ | 5.9 (m,1H, $-CH=$), 5.25 (m,2H, $=CH_2$) |
| 32 | $C_2H_5-$ | $-CH_2-CH=CH-CH_3$ | $-C_2H_5$ | 5.45–5.8 (2m,2H, $-CH=CH-$) |
| 33 | $C_2H_5-$ | $-CH_2-CH=CH_2$ | $-CH_2-CH=CH-CH_3$ | 5.2 (m,2H, $=CH_2$) |

-continued

Examples $$R^1-O-\underset{\underset{O}{\|}}{\overset{R^2}{C}}-\underset{}{N}-O-R^3$$

| Ex. | R¹ | R² | R³ | ¹H-NMR Data (ppm) |
|---|---|---|---|---|
| 34 | C₂H₅— | —CH₂—C≡CH | —CH₂—CH₂—CH₃ | 3.8 (t,2H,OCH₂—CH₃), 2.3 (t,1H,≡CH) |
| 35 | C₂H₅— | —CH₂—CH=CH₂ | —CH₂—CH₂—CH₃ | 5.9 (m,1H,—CH=), 3.8 (t,2H,CH₃—CH₂—), |
| 36 | C₆H₅—CH₂ | —CH₂—C≡CH | —CH₃ | 4.25 (d,2H,—N—CH₂—), 2.3 (t,1H,≡CH) |
| 37 | C₂H₅— | —CH₂—CH=CH₂ | —(CH₂)₄—CH₃ | 5.8–6 (m,1H,—CH=), 3.85 (t,2H,Eto) |
| 38 | C₂H₅— | —CH₂—C≡CH | —(CH₂)₃—CH₃ | 3.9 (t,2H,CH₃—CH₂—O), 2.3 (t,1H,≡CH) |
| 39 | C₂H₅— | —CH₂—C≡CH | —CH₂—CH(CH₃)—CH₂ | 4.25 (d,2H,—N—CH₂—), 2.3 (t,1H,≡CH) |
| 40 | C₂H₅— | —CH₂—CH=CH—CH₃ | —CH₂—CH₂—CH₃ | 5.5–5.75 (2m,2H,—CH=CH—) |
| 41 | CH₃— | —CH₂—C≡CH | —CH₂—CH₂—CH₃ | 3.8 (s,3H,—OCH₃), 2.25 (t,1H,≡CH) |
| 42 | CH₃— | —CH₂—CH=CH₂ | —CH₂—CH₂—CH₃ | 5.9 (m,1H,—CH=), 3.8 (s,3H,—O—CH₃) |
| 43 | CH₃— | —CH₂—CH=CH—CH₃ | —CH₂—CH₂—CH₃ | 5.45–5.75 (2m,2H,—CH=CH—) |
| 44 | CH₃— | —CH₂—C≡CH | —CH₂—CH₂—CH₂—CH₃ | 3.8 (s,3H,—OCH₃), 2.3 (t,1H,≡CH) |
| 45 | CH₃— | —CH₂—CH=CH₂ | —(CH₂)₃—CH₃ | 5.9 (m,1H,—CH=), 3.75 (s,1H,CH₃O) |
| 46 | C₂H₅— | —CH₂—CH=CH₂ | —(CH₂)₃—CH₃ | 5.9 (1H,m,—CH=), 4.2 (q,2H,CH₃—CH₂—O) |
| 47 | C₂H₅— | —CH₂—CH=CH—CH₃ | —(CH₂)₃—CH₃ | 3.5–5.8 (2m,2H,—CH=CH—) |
| 48 | C₂H₅— | —CH₂—CH=CH—CH₃ | —(CH₂)₄—CH₃ | 5.5–5.8 (2m,2H,—CH=CH—) |
| 49 | CH₃— | —CH₂—CH=CH—CH₃ | —(CH₂)₃—CH₃ | 5.5–5.8 (2m,2H,—CH=CH—), 3.8(s,3H,CH₃O) |
| 50 | CH₃— | —CH₂—C≡CH | —C₂H₅ | 3.8 (s,3H,CH₃O), 2.25 (t,3H,≡CH) |
| 51 | CH₃— | —CH₂—CH=CH₂ | —C₂H₅ | 5.9 (m,1H,—CH=), 3.8 (s,3H,CH₃O) |
| 52 | CH₃— | —CH₂—C≡CH | —(CH₂)₄—CH₃ | 3.8 (s,3H,CH₃O), 2.2 (t,3H,≡CH) |
| 53 | CH₃— | —CH₂—CH=CH₂ | —(CH₂)₄—CH₃ | 5.9 (m,1H,—CH=), 3.7 (s,3H,CH₃O) |
| 54 | CH₃— | —CH₂—CH=CH—CH₃ | —(CH₂)₄—CH₃ | 5.45–5.75 (2m,2H,—CH=CH—) |
| 55 | C₂H₅— | —CH₂—CH=CH₂ | —CH₂—CH(CH₃)₂ | 5.9 (m,1H,—CH=), 0.95 (d,6H,CH(CH₃)₂) |
| 56 | C₂H₅— | —CH₂—CH=CH—CH₃ | —CH₂—CH(CH₃)₂ | 1.9 (hept.,1H,—CH(CH₃)₂), 0.95 (d,6H,CH(CH₃)₂) |
| 57 | CH₃— | —CH₂—C≡CH | —CH₂—CH(CH₃)₂ | 3.8 (s,3H,—OCH₃), 2.25 (t,1H,≡CH) |
| 58 | CH₃— | —CH₂—C≡CH | —CH₂—CCl=CH₂ | 3.8 (s,3H,—OCH₃), 2.25 (t,1H,≡CH) |
| 59 | CH₃— | —CH₂—CH=CH₂ | —CH₂—CCl=CH₂ | 3.8 (s,3H,—OCH₃), 5.9 (m,1H—CH=) |
| 60 | CH₃— | —CH₂—CH=CH—CH₃ | —CH₂—CCl=CH₂ | 3.8 (s,3H,—OCH₃) |
| 61 | C₂H₅— | —CH₂—C≡CH | —CH₂—CCl=CH₂ | 4.5 (s,2H,—N—O—CH₂—), 2.3 (t,1N,≡CH) |
| 62 | C₂H₅— | —CH₂—CH=CH₂ | —CH₂—CCl=CH₂ | 5.9 (m,1H,—CH=), 1.3 (t, 3H,CH₃—CH₂—O) |
| 63 | C₂H₅— | —CH₂—CH=CH—CH₃ | —CH₂—CCl=CH₂ | 4.4(s,2H,—N—O—CH₂), 1.3(t,3H,CH₃—CH₂—O) |
| 64 | C₂H₅— | —CH₂—CCl=CH₂ | —CH₂—CCl=CH₂ | 1.3 (t,3H,CH₃—CH₂—O) |
| 65 | C₂H₅— | —CH₂—CCl—CH₂ | —CH₂—CH₂—CH₃ | 1.0 (t,3H) 1.3 (t,3H), 1.7 (m,2H), 4.2 (m,2H), 4.91 (m,2H) |
| 66 | C₂H₅— | —CH₂—CH=CHCl | —CH₂—CH₂—CH₃ | 1.0 (t,3H) 1.3 (t,3H) 1.6 (m,2H) 6.0 (m, 1H), 6.2 (m,1H) |
| 67 | C₂H₅— | —CH₂—CH₂—CH₃ | —CH₂—C≡CH | 0.95 (t,3H) 1.3 (t,3H), 2.5 (t, 1H) 4.5 (d, 2H) |
| 68 | C₂H₅— | —CH₂—CH=CH—CH₃ | —CH₂—C≡CH | 1.3 (t,3H) 1.7 (m,3H) 2.5 (t,1H) 5.5 (m,1H) 5.6 (m,1H) |
| 69 | C₂H₅— | —CH₂—CCl=CH₂ | —CH₂—C≡CH | 1.3 (t,3H) 2.5 (t,1H) 5.35 (d,2H) |
| 70 | C₂H₅— | —CH₂—C≡C—CH₂Cl | —C₂H₅ | |
| 71 | C₂H₅— | —(CH₂)₃—CH₃ | —CH₂—C≡CH | 0.9 (t,3H) 1.3 (t,3H) 1.58 (m,2H) 2.5 (t,1H) 3.6 (t,2) 4.2 (m,2H) 4.5 (d,2H) |
| 72 | C₂H₅— | —CH₂—CH₂—CH₂—Cl | —CH₂—CH=CH₂ | 1.3 (t,3H) 4.13 (m,2H) 5.3 (m,2H), 5.95 (m,1H) |
| 73 | CH₃— | —CH₂—CH₂—CH₂—Cl | —CH₂—C≡CH | 2.55 (t,1H), 3.8 (s,3H), 4.52 (d,2H) |
| 74 | C₂H₅— | —CH₂—CH₂—CH₂—Cl | —CH₂—CCl=CH₂ | 1.35 (t,3H) 2.13 (m,2H), 3.5–3.75 (m, 4H) 4.22 (m2H) 4.45 (s,2H) 5.5 (d,24) |
| 75 | C₂H₅— | —CH₂—C≡CH | —CH₃ | 1.35 (t,3H) 2.3 (t,1H) 3.7 (s,3H) 4.15–4.13 (m,4H) |
| 76 | CH₃— | —CH₂—C≡CH | —CH₃ | 2.3 (t,1H), 3.7 (d,6H), 4.25 (d,2H) |
| 77 | C₂H₅— | —CH₂—C≡CH | 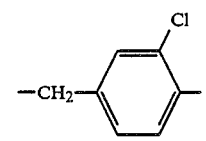 | 1.35 (t,3H) 2.3 (t,1H) 4.2–4.35 (m,4H) 4.95 (s,2H) 7.1–7.5 (m,4H) |
| 78 | C₂H₅— | —CH₂—CH=CH₂ | 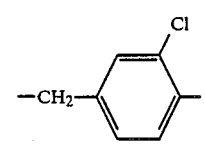 | 1.3 (t,3H), 4.0 (m,2H) 4.2 (2H) 4.83 (s,2H) 5.8–5.9 (m,1H) 7.1–7.5 (m,4H) |
| 79 | C₂H₅— | —CH₂—C≡CH | 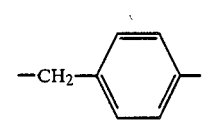 | 1.3 (t,3H) 2.25 (t,1H) 2.35 (s,3H) 4.15 (d,2H) 4.22 (m,2H) 4.92 (s,2H) 7.18 (d, 2H) 7.32 (d,2H) |

What is claimed is:

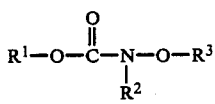     I in which
- $R^1$ represents $C_{1-20}$-alkyl, $C_{2-20}$-alkenyl, $C_{3-20}$-cycloalkyl, $C_{2-20}$-alkinyl, phenyl or naphthyl, optionally substituted by alkyl with 1 to 4 carbon atoms; alkoxy with 1 to 4 carbon atoms; alkylthio with 1 to 4 carbon atoms; halogeno-alkyl with 1 to 4 carbon atoms and 1 to 5 halogen atoms; halogenoalkoxy with 1 to 4 carbon atoms and 1 to 5 halogen atoms; halogenoalkylthio with 1 to 4 carbon atoms and 1 to 5 halogen atoms; in the case of phenyl, for alkylenedioxy with 1 or 2 carbon atoms and for halogen-substituted alkylenedioxy with 1 or 2 carbon atoms and 1 to 4 halogen atoms; halogen; cyano; nitro; dialkylamino with 1 to 4 carbon atoms per alkyl group; alkylcarbonyl with 2-4 carbon atoms; carbalkoxy with 2 to 4 carbon atoms; alkylsulphonyl with 1 to 4 carbon atoms; arylsulphonyl with 6 or 10 aryl carbon atoms; phenyl, naphthyl, phenoxy, naphthoxy, phenylthio and naphthylthio,
- $R^2$ represents $C_{1-6}$-alkyl, $C_{2-6}$-alkenyl or $C_{2-6}$-alkinyl, which can optionally be substituted by halogen, and
- $R^3$ represents $C_{1-6}$-alkyl, $C_{2-6}$-alkenyl or $C_{2-6}$-alkinyl, which can optionally be substituted by halogen, at least one of $R^2$ and $R^3$ being alkinyl.

2. The method according to claim 1, wherein at least one of $R^2$ and $R^3$ is propargyl.

3. A method according to claim 1, in which
- $R^1$ represents methyl or ethyl, benzyl or phenyl which is optionally substituted by halogen, $NO_2$, $CF_3$, $OCF_3$, $SCF_3$, $SCF_2Cl$, $OCH_3$, $OCF_2CF_2H$, $-OCF_2-CHFO-$, $-O-CH_2-O$ or $O-CF_2-O$,
- $R^2$ represents methyl, ethyl, n-propyl, i-propyl, butyl, pentyl, allyl, 3-chloro-prop-2-enyl, 2-chloro-prop-2-enyl, 3,3-dichloroprop-2-enyl, but-2-enyl or propargyl and
- $R^3$ independently of $R^2$ represents the radicals mentioned for $R^2$.

4. The method according to claim 1, wherein such ester is N-propargyl-N-propargyloxy ethyl carbamate of the formula

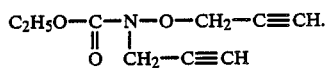

5. The method according to claim 1, wherein such ester is N-propargyl-N-propargyloxy methyl carbamate of the formula

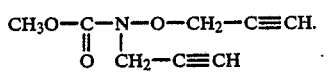

6. The method according to claim 1, wherein such ester is N-propargyl-N-ethoxy ethyl carbamate of the formula

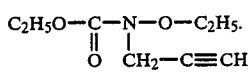

7. The method according to claim 1, wherein such ester is N-propargyl-N-n-propoxy ethyl carbamate of the formula

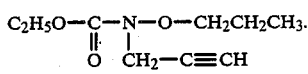

8. The method according to claim 1, wherein such ester is N-propargyl-N-n-propoxy methyl carbamate of the formula

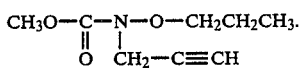

* * * * *

UNITED STATES PATENT AND TRADEMARK OFFICE
CERTIFICATE OF CORRECTION

PATENT NO. : 4,914,124

DATED : April 3, 1990

INVENTOR(S) : Muller, et al.

It is certified that error appears in the above-identified patent and that said Letters Patent is hereby corrected as shown below:

Col. 23, claim 1 line 1    Add on line 1 before formula -- A method of combating endoparasites which comprises applying thereto or to an endoparasite habitat an endoparasiticidally effective amount of an N-organooxycarbamic acid ester of the formula --

Signed and Sealed this

Twenty-ninth Day of October, 1991

Attest:

HARRY F. MANBECK, JR.

*Attesting Officer*     *Commissioner of Patents and Trademarks*